(12) United States Patent
Sahiri et al.

(10) Patent No.: US 8,351,030 B2
(45) Date of Patent: Jan. 8, 2013

(54) METHOD AND DEVICE FOR PRODUCING A CUVETTE AND CUVETTE PRODUCED USING SAID METHOD

(75) Inventors: Thomas Sahiri, Calabasas, CA (US); Werner Schneider, Chamerau (DE)

(73) Assignee: Thomas Sahiri, Calabasas, CA (US)

( * ) Notice: Subject to any disclaimer, the term of this patent is extended or adjusted under 35 U.S.C. 154(b) by 336 days.

(21) Appl. No.: 12/671,079

(22) PCT Filed: Oct. 1, 2008

(86) PCT No.: PCT/EP2008/008331
§ 371 (c)(1), (2), (4) Date: Jan. 28, 2010

(87) PCT Pub. No.: WO2009/046924
PCT Pub. Date: Apr. 16, 2009

(65) Prior Publication Data
US 2010/0182597 A1    Jul. 22, 2010

(30) Foreign Application Priority Data
Oct. 8, 2007    (DE) .......................... 10 2007 048 211

(51) Int. Cl.
*G01N 1/10*    (2006.01)
(52) U.S. Cl. ....................................... 356/246; 356/244
(58) Field of Classification Search .................. 356/246
See application file for complete search history.

(56) References Cited

U.S. PATENT DOCUMENTS
6,249,345 B1 *  6/2001  Kraack et al. ................. 356/246
2001/0015512 A1  8/2001  Fontana

FOREIGN PATENT DOCUMENTS

| | | |
|---|---|---|
| DE | 17729 | 4/1882 |
| DE | 19826470 | 12/1999 |
| EP | 0668496 | 2/1995 |
| EP | 1215479 | 6/2002 |
| GB | 909555 | 10/1962 |
| JP | 5257257 | 5/1977 |
| JP | 5458761 | 5/1979 |
| JP | 08011171 | 1/1996 |

OTHER PUBLICATIONS

Sors, L., "Spritzgiesswerkzeug Fuer Fluessigkeits—Messylinder", Kunststoffe, Carl Hanser Verlag, Munche, Germany, vol. 68, No. 9, Sep. 1, 1978, p. 523, Figure 1.

* cited by examiner

*Primary Examiner* — Tara S Pajoohi Gomez
(74) *Attorney, Agent, or Firm* — Volpe and Koenig, P.C.

(57) ABSTRACT

A multi-part injection mold (10) for producing a cuvette (1) or a receptacle vessel for liquid or gaseous media for spectroscopic, qualitative and/or quantitative analysis or measurement using a measuring region or measuring gap (2) through which radiation is able to penetrate is provided, with the cuvette being made of plastic through injection molding. To this end, the inner cavity or filling space (9) and the measuring gap (2) are formed and limited on the interior of the injection mold (10) by a contour core (11), the thickness of which is limited to about one millimeter or less in the region (11a) of the measuring gap (2). The contour core (11) is held on the end (11b) thereof having the smallest dimension during the injection molding process, initially by at least one support (14), and retracted during the injection molding process after partial filling of the mold with plastic such that the lower continuation of the walls of the measuring gap (2) is formed.

10 Claims, 4 Drawing Sheets

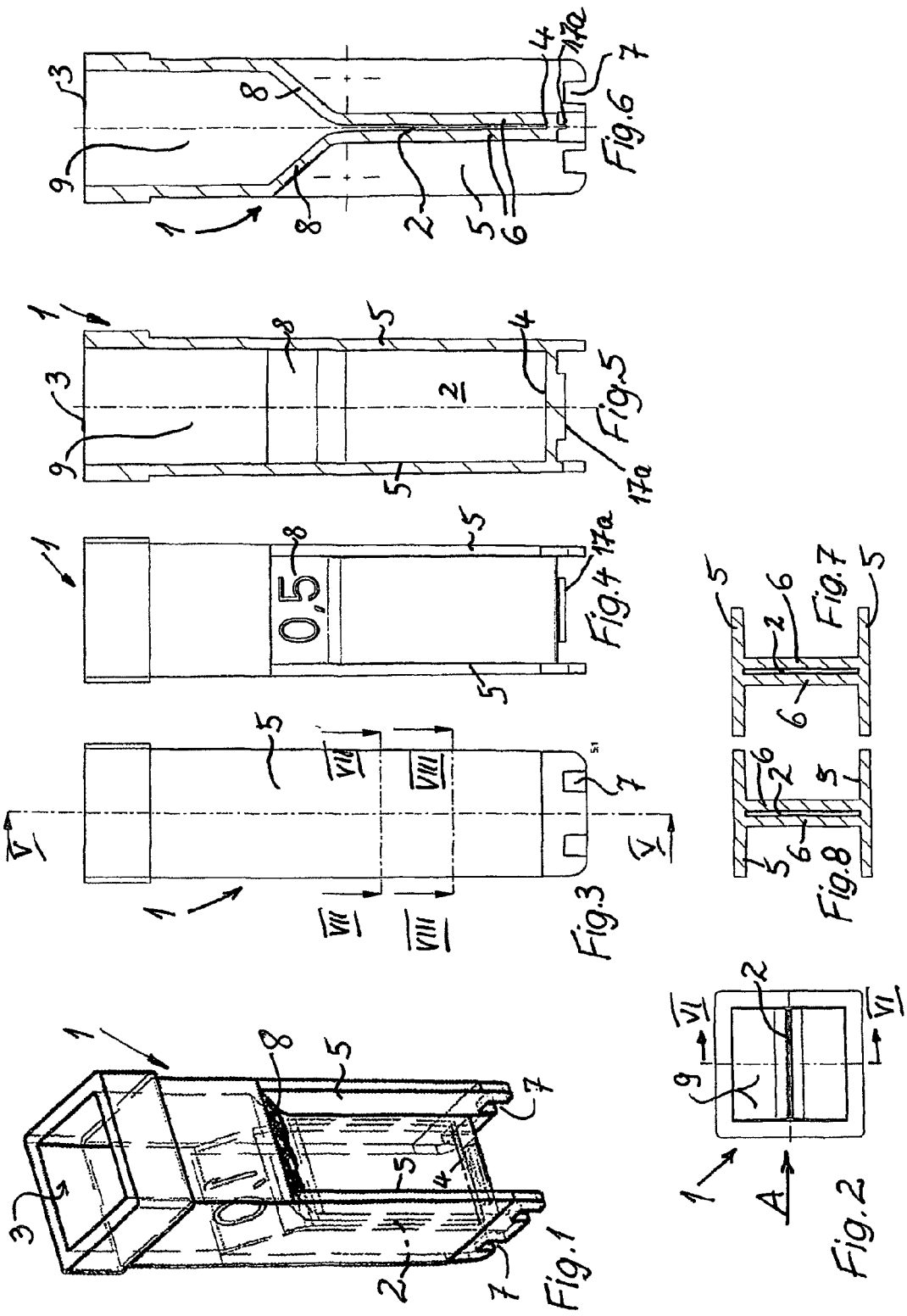

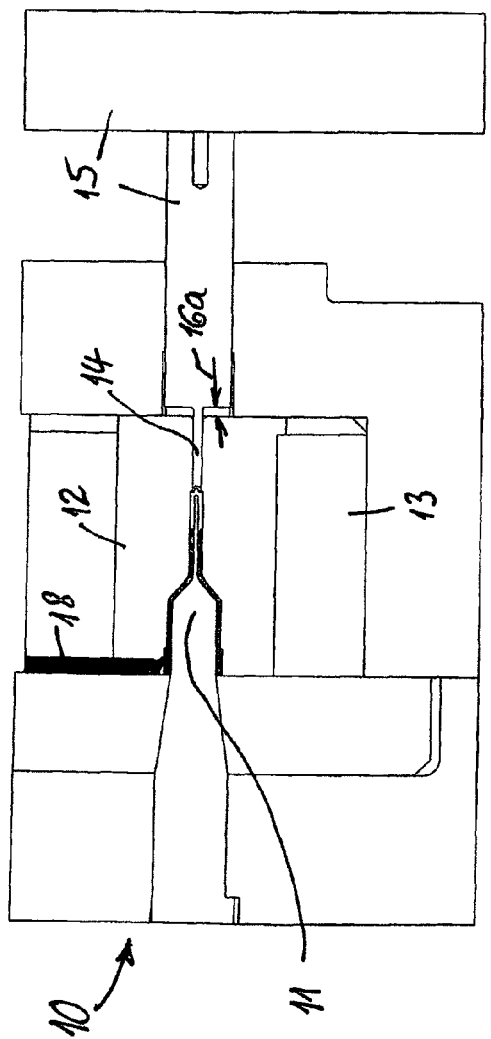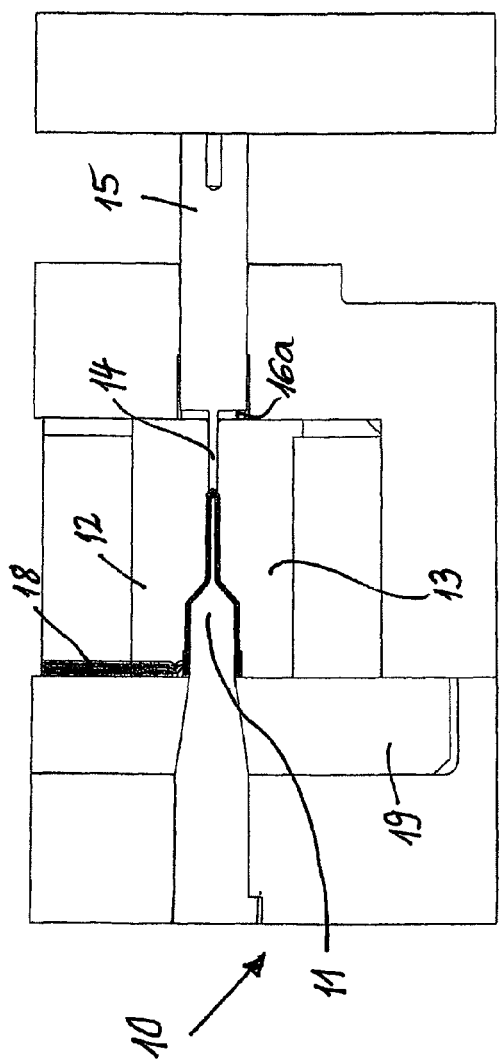

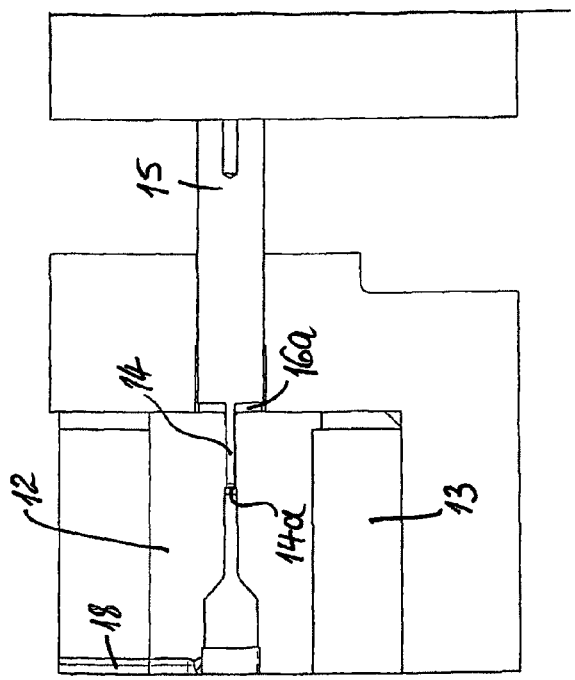
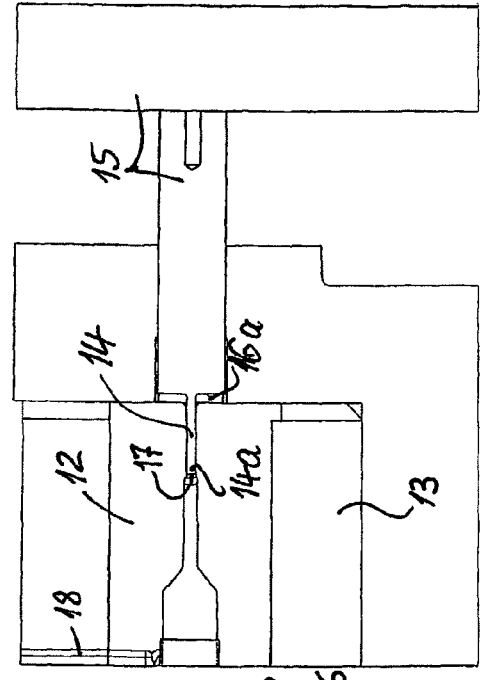
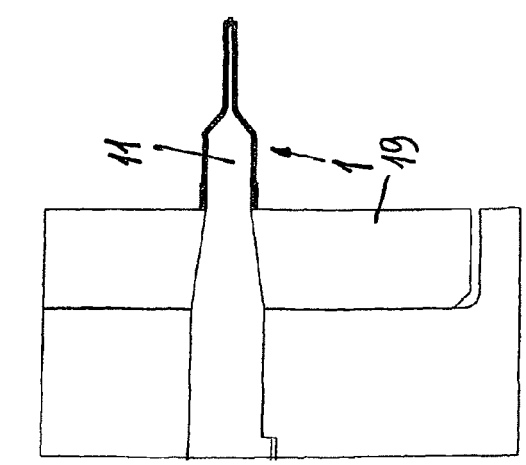
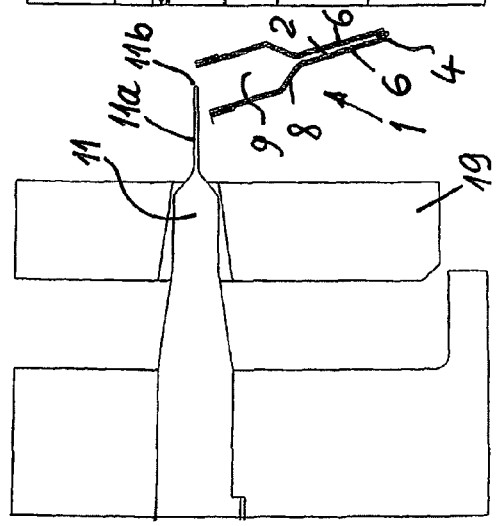

METHOD AND DEVICE FOR PRODUCING A CUVETTE AND CUVETTE PRODUCED USING SAID METHOD

BACKGROUND

The invention relates to a method for producing a cuvette or a receptacle vessel for liquid or gaseous media for spectroscopic, qualitative, and/or quantitative analysis or measurement having a measuring region or measuring gap that can be penetrated by radiation and is made from plastic by way of injection molding, with a multi-part injection mold, comprising in the interior the contour of the cuvette or the receptacle vessel with its opening and measuring gap, is first filled with liquid plastic in an injection molding device and after the plastic has set the mold is opened and the cuvette is removed, with in the mold the interior longitudinal cavity and the measuring gap are formed and limited at the inside by a contour core, which during the molding process initially is held by a support.

Such cuvettes made from plastic, but also from quartz glass, are known in various shapes and dimensions, particularly with regard to the thickness of the measuring gap, also called layer thickness. For example, a plastic cuvette is known from DE 198 26 470 A1 having a particular embodiment, comprising two pairs of opposite coplanar windows in order to allow different layer thicknesses.

A layer thickness as low as possible, i.e. a measuring gap with a thickness as low as possible, results in a considerable shortening of the radiation path, which is advantageous for the accuracy of the measurement.

In quartz cuvettes, layer thicknesses of one millimeter or less are possible due to the method of production, however, producing plastic cuvettes with a layer thickness of less than two millimeters was previously impossible so that either a relatively high layer thickness had to be accepted or a very expensive quartz cuvette had to be used, which is not suitable for single use, though, due to its high production costs.

SUMMARY

Therefore, the object is to provide a method and a device for producing a cuvette and/or a receptacle vessel of the type mentioned at the outset made from plastic, thus allowing low production costs in order to also allow the use of the plastic cuvette as a single use item, having a lower layer thickness and correspondingly allowing good measurements.

In order to attain this objective, the method defined at the outset is characterized in that the thickness of the contour core is limited to one millimeter or less in the region of the measuring gap, that the contour core is held by the support at its end comprising the smallest dimension, and that the end of the measuring gap facing away from the opening of the vessel or the cuvette is formed such that during the molding process the support is removed or retracted from the contour core, with the support together with the end of the contour core forming the lower limit or continuation of the walls of the measuring gap at its end, and that the molding process is continued during or after the removal or retraction of the support until the hollow space thus released has been filled, with the support for the contour core forming the measuring gap being retracted in the direction of the initial extension of the measuring gap and perpendicularly in reference to the later alignment of the radiation.

In this manner, a plastic cuvette with a very low layer thickness of one millimeter or less can be produced, in order to achieve the automatic physical dilution of the samples by shortening the radiation path. In order to prevent the very thin contour core from being deformed or deflected by the plastic injected into the mold, which would result in the measuring gap failing to form or developing in a wrong form or position, the very thin contour core is first held with a support in the desired position until sufficient plastic has been injected at both sides of said contour core, and subsequently the support is retracted to such an extent that the limit of the molding of the measuring gap can be completed.

In this way, a plastic cuvette with a very low layer thickness can be produced such that the advantages of the low layer thickness can be achieved with comparatively low production costs, and the cuvette with such a low layer thickness can still be made from plastic as a single use item. Depending on the plastic used, this cuvette can be used both for visible light as well as the UV-light range.

In the method according to the invention it is advantageous that the support together with the end of the contour core forms the lower continuation of the wall of the measuring gap at its end, i.e. the lower limit of the measuring gap, and that the molding process, after the limited retraction of the support, is continued until the hollow space released thereby is completely filled. The hollow space released during the removal or retraction is here formed or selected due to the extent of the retraction and also the shape of the contour core at the side facing the support such that the lower limit of the measuring gap or a place of the wall of the measuring gap, initially interrupted by the support, is complemented and filled out.

Due to the fact that the support for the contour core initially forming the measuring gap is moved away or retracted in the direction of extension of the measuring gap perpendicular in reference to the later alignment of the radiation, with the initially still supported contour core, the plastic can fill the intermediate space between the contour core and the other molded parts at both sides of the contour core later forming the walls of the measuring gap, resulting after a certain fill level in the contour area being stabilized due to its inert stability and the plastic located at both sides such that during the further filling process no deflection of the contour core occurs. Then, at least one support can be retracted and thus also release the region for filling in plastic, which was initially blocked by the support and beneficially has limited the lower end of the measuring gap and thus plastic was blocked from entering by at least one support.

It is beneficial when the support, arranged as a narrow intermediate piece between the form parts, forming the exterior of the vessel or the cuvette, is moved away or retracted from the contour core in the separating region of the two mold parts, and subsequently the injection molding process is concluded.

The invention also relates to a device for producing a cuvette or a receptacle vessel for liquid or gaseous media for spectroscopic qualitative and/or quantitative analysis or measurement with a measuring region or measuring gap, that can be penetrated by radiation, made from plastic by way of injection molding and used to attain the above-mentioned object, characterized in that it comprises a multi-part injection mold, with the exterior contour of the cuvette being arranged in a cavity of a mold or between two mold parts and the interior contour with the measuring gap of the cuvette being formed by a contour core, which is arranged in the mold or between the two mold parts, and which has a narrow region located inside the injection mold for forming the measuring gap, which contour core showing a cross-sectional thickness of one millimeter or less plus or minus tolerances, and that at least one support of the free narrow end of the contour core being arranged retractably inside the mold in reference to the contour core in the direction of extension of the narrow part of the contour core, which during the filling process of the mold with liquid plastic can be retracted particularly by the wall thickness of the limit of the interior or lower end of the measuring gap or to a lesser extent and that the support is embodied as a core-like intermediate piece between the mold parts and fills a distance between these mold parts, with said distance being arranged adjacent to the distance of the mold parts which the contour core engages is the operational position.

By such a device, essentially formed by an injection mold, the cuvette or the receptacle vessel can be produced in an injection molding process with a very narrowly sized measuring gap because the contour core, primarily forming the very thin or narrow measuring gap of one millimeter thickness or less, first being supported during the injection of plastic into the mold and thus being hindered from an undesired deformation or deflection, with the support of the contour core having a dual function, because after a certain period of time it can be retracted and subsequently the exterior of the lower end of the measuring gap is formed or molded.

Due to the fact that the support is embodied as a core-like intermediate piece between the mold parts and fills a space between said mold parts, arranged adjacent to the space of the mold parts with the contour core engaging in the operational position the two essential mold parts of the injection mold which are spaced apart over the entire extension of the measuring gap and in this space, on the one side, the contour core is located and, on the other side, also the support, with the support initially filling this space such that it is ensured that plastic can only be injected into the area forming the walls of the measuring gap between the contour core and the mold parts.

The support of the contour core may comprise a concave or groove-like recess at its supporting end, which accepts the edge of the contour core when supporting or it encapsulates it in a form-fitting manner, and which forms the exterior contour of the limiting wall of the measuring gap at its interior or lower end. By such an approximately groove-shaped or concave recess or indentation at the supporting end of the support the contour core can be grasped at its essentially free end in a form-fitting fashion and accordingly can be securely positioned, while the first larger part of the plastic mass is injected into the mold. Accordingly, the contour core is held safely and dimensionally stable in spite of its low thickness. Additionally, this embodiment of the support results in a characteristic exterior end of the limit of the measuring gap at its interior or lower end and also in a sufficient thickness of said transition between the two limiting walls of the measuring gap.

Here it is beneficial when the thickness of the support is lower by a fraction of the thickness of the walls limiting the measuring gap than the distance of the mold parts forming the exterior sides of the walls of the measuring gap or a slot forming the region of the measuring gap in a mold part. Due to the fact that the support forms a corresponding distance of the mold parts, i.e. in the region in which the support device is located first, the distance of the mold parts is slightly less than in the region of the rest of the contour core, with said transition of the distance being arranged in the region of the end of the measuring gap such that first the support core engaging here together with the stop forms a limit between these slightly differently measured distances, through which no plastic can exit. Due to the fact that during the injection molding process the support, i.e. the support core, is retracted to such an extent that the transition of the two walls limiting the measuring gap can also be filled with plastic, at the end of the measuring gap a limit made from plastic also forms, with the retraction of the support being approximately equivalent to the overlapping of the region of the greater distance to the initially not yet retracted support.

The object defined at the outset and here primarily the shortening of the radiation path within a cuvette or a receptacle vessel made from plastic is attained in a cuvette or a receptacle vessel for liquid or gaseous media for spectroscopic qualitative and/or quantitative analysis or measurement using a measuring region or measuring gap made from plastic that can be penetrated by radiation such that the thickness of the measuring gap amounts to approximately one millimeter plus or minus a slight tolerance or less, for example half a millimeter. Plastic cuvettes with such a small dimensioned measuring gap have considerable advantages for respective measuring processes due to the physical dilution of the samples examined and yet they can still be used as single use items due to their manufacturing from plastic.

Here it is beneficial for the measuring gap to show a tapering form at the end in the direction facing away from the opening of the cuvette and the cross-sectional thickness, i.e. the dimension in the direction of the measuring radiation, amounts to approximately 1.05 millimeter or tapering from approximately 1.003 millimeter to approximately 0.95 millimeter or 0.96 millimeter, or respectively an interim value plus or minus a tolerance of approximately five one-hundredths of a millimeter or half a millimeter and from approximately 0.52 millimeter to 0.517 millimeter to 0.45 millimeter with a tolerance of two and one half one-hundredths of a millimeter.

Accordingly, an embodiment of the device according to the invention may also provide for the contour core comprising the above-mentioned dimensions having a slightly conical shape in order to facilitate the ejection after the conclusion of the injection molding process. The above-mentioned slight measurement deviations in the progression of the measuring gap have no influence on the measurement, here, because they are so small; however the ejection is facilitated.

According to the invention, a cuvette is provided produced with a method and/or a device as explained above, with the cross-sectional thickness of the contour core may comprise approximately one millimeter or approximately one half of one millimeter plus or minus the above-mentioned tolerances.

Primarily when both the cuvettes, showing a measuring gap with a thickness of one millimeter as well as showing a measuring gap of only one half of one millimeter thickness, are provided as a cuvette set it may be beneficial when at a wall, a flange, or an edge, for the purpose of marking different gap widths of the measuring gap, different numbers and/or differently shaped geometric numbers, grooves, notches, recesses, or indentations may be provided for differentiating the variously sized cuvettes, which may be detected, for example, by sensors, detectors, or probes of a measuring device accepting such cuvettes, so that automatically during measuring the corresponding thickness of the measuring gap is considered for the measurement or can be included in the calculation. This beneficial embodiment for marking different cuvettes is advantageously possible because the cuvettes can be produced according to the invention from plastic in spite of their low thickness of the measuring gap.

Another embodiment may here provide that the central height of the cuvette amounts from one half to three centimeters, particularly from three fourth of a centimeter to two and one half centimeters, preferably from eight millimeters to two centimeters. The cuvettes can be used accordingly for a multitude of purposes without requiring any adapters.

BRIEF DESCRIPTION OF THE DRAWINGS

In the following, exemplary embodiments of the invention are described using the drawing. Shown in a partially schematic representation are:

FIG. 1 a schematic side view of a cuvette according to the invention with an inversely visible marking "1.0" as an indication for a thickness of the measuring gap amounting to one millimeter, FIG. 2 a top view of the cuvette according to FIG. 1, FIG. 3 a side view of the cuvette according to the invention in the direction of view of the arrow A in FIG. 2, FIG. 4 a side view of the cuvette according to the invention rotated by 90° with the marking "0.5" as an indication for a thickness of the measuring gap amounting to 0.5 millimeter;

FIG. 5 a longitudinal cross-sectional view of the cuvette according to the sectional line V-V in FIG. 3, FIG. 6 a longitudinal cross-sectional view of the cuvette according to the invention perpendicular in reference to the measuring gap according to the sectional line VI-VI in FIG. 2, FIG. 7 a cross-sectional view of the cuvette in the region of the measuring gap according to the sectional line VII-VII in FIG. 3, FIG. 8 a cross-sectional view of the cuvette approximately equivalent to FIG. 7, however at a slightly lower point of the measuring gap according to the sectional line VIII-VIII in FIG. 3, FIG. 9 in a more schematic illustration, a longitudinal cross-sectional view through a device embodied as an injection mold comprising several mold parts for the production of the plastic cuvette shown in FIGS. 1 through 8, with a contour core being provided between two mold parts forming the exterior walls of the measuring gap and their continuations to form the opening and the interior of the cuvette including the measuring gap and a support for the end of said contour core, FIG. 10 an illustration according to FIG. 9 after a part of the hollow space formed by the injection mold and the contour core has been filled, with the support still contacting and supporting the contour core, FIG. 11 an illustration according to FIG. 10, with the support being retracted from the end of the contour core by approximately the thickness of the transition between the walls limiting the measuring gap and thus releasing the connection of these two walls, FIG. 12 an illustration according to FIG. 11 after the space has been completely filled with plastic, also released by the retraction of the support inside the injection mold, FIG. 13 a view of the first step of the ejection, in which the mold parts forming the exterior sides of the cuvette are off-set in reference to the other parts of the injection mold and particularly in reference to the finished cuvette, releasing it, by for example retracting the mold parts forming the interior of the cuvette together therewith, as well as FIG. 14 a view according to FIG. 13, with a doctor, adjustable in reference to the contour core in its direction of extension, which initially forms simultaneously the opening edge of the cuvette at the face, and is moved forward in reference to the contour core, and thus removes the finished cuvette from the contour core.

DETAILED DESCRIPTION OF THE PREFERRED EMBODIMENTS

Figure 9:
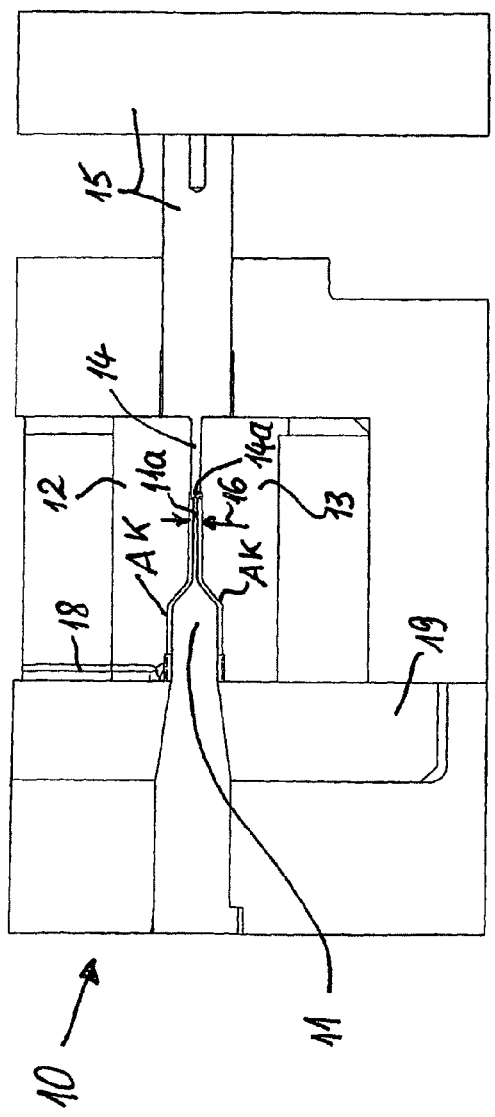

A cuvette, in the following in its entirety marked 1, serves in a manner known per se to accept liquid or gaseous media for spectroscopic quantitative and/or qualitative analyses or measurements, even when showing different dimensions of the measuring gap, and for this purpose it has a measuring region or measuring gap 2 that can be penetrated by radiation, with its thickness according to the marking in FIG. 1 amounts to one millimeter plus or minus tolerances or less, for example according to FIG. 4, half a millimeter plus or minus tolerances.

For this purpose, the cuvette 1 is made from plastic, although the measuring gap 2 is measured such small. Here, it is indicated in FIGS. 6 through 8, that the measuring gap 2 has a shape tapering at the end 4 of the cuvette 1 facing away from the direction of the opening 3, with the cross-sectional thickness of said measuring gap 2 amounting to approximately 1.05 millimeter or from approximately 1.03 millimeter to approximately 0.95 millimeter or to approximately 0.96 millimeter or a respective intermediate value plus or minus a tolerance of approximately five one-hundredths of a millimeter, if it represents a cuvette according to FIG. 1 showing the marking "1.0." In a cuvette 1 having the marking "0.5" the measuring gap 2 and its tapering shape may have a cross-sectional thickness of approximately 0.52 millimeter or 0.517 millimeter, which reduces to 0.45 millimeter with a tolerance of two and one half hundredths of a millimeter. This slightly conical shape of the measuring gap 2 allows and facilitates the ejection of a contour core 11, arranged in a device or injection mold 10 serving for the production of the cuvette 1 and yet to be described, which is shown particularly clearly in FIG. 14.

Here, it is discernible in FIGS. 1, 3, and 6 that at one or two walls 5, arranged perpendicularly in reference to the extension of the measuring gap 2 and the walls 6 limiting them, for marking different gap widths or dimensions of the measuring gap 2, for example different numbers and/or differently shaped geometric signs, grooves, notches, recesses, or indentations 7 are provided for differentiating the differently sized cuvettes 1. This allows to facilitate the differentiation of the cuvettes and to render it independent from labeling, so that sensors or other means, for example electronic or mechanic detectors, may also recognize what type of cuvette 1 is given, with the respective dimension of the gap width.

Here, it is also discernible, primarily in FIGS. 1 and 6, that the cuvette 1 may show a large central height, which is also facilitated by the slightly conical shape of the measuring gap 2 and/or the contour core 11 forming it and remaining to be explained in detail. This central height may amount from one half to three centimeters, particularly from three quarters of a centimeter to two and one half centimeters, preferably approximately from eight millimeters to two centimeters and thus allowing a multitude of applications for the cuvette 1.

Primarily in FIGS. 1, 2, and 6 it is additionally discernible that the walls 6 limiting the measuring gap 2 transition via diagonal surfaces 8 into an approximately box-shaped fill chamber 9, located below the opening 3, and/or a liquid, injected through the opening 3 and filling the fill chamber 9, enters it via the diagonal surface 8 through the capillary effect of the low thickness of the measuring gap 2 such that a measurement is possible free from bubbles.

FIGS. 9 through 14 schematically show a device 10, according to which the production of the cuvette 1 is explained in the following.

The device 10 is a multi-part injection mold, by which the cuvette 1 can be produced from plastic via injection molding. Here, it is first discernible in FIG. 9 that the exterior contour AK of the cuvette 1 is arranged between two mold parts 12 and 13 and is formed by them and that the interior contour, i.e. essentially the fill chamber 9, the transition, and the measuring gap 2 are formed by the above-mentioned contour core 11, with said contour core 11 being arranged between the two mold parts 12 and 13 and maintain a distance 16, equivalent to the wall thickness of the cuvette in the region of the fill chamber 9, the transition at the diagonal surface 8, and the measuring gap 2.

Here, it is also discernible primarily in FIG. 14 that this contour core 11 has a narrow region 11a for forming the measuring gap 2, located inside the injection mold 10, which contour core 11 has a cross-sectional thickness in said narrow region 11a, which is equivalent to the thickness of the measuring gap 2, i.e. amounting approximately to one millimeter or less plus or minus tolerances.

Figure 10:
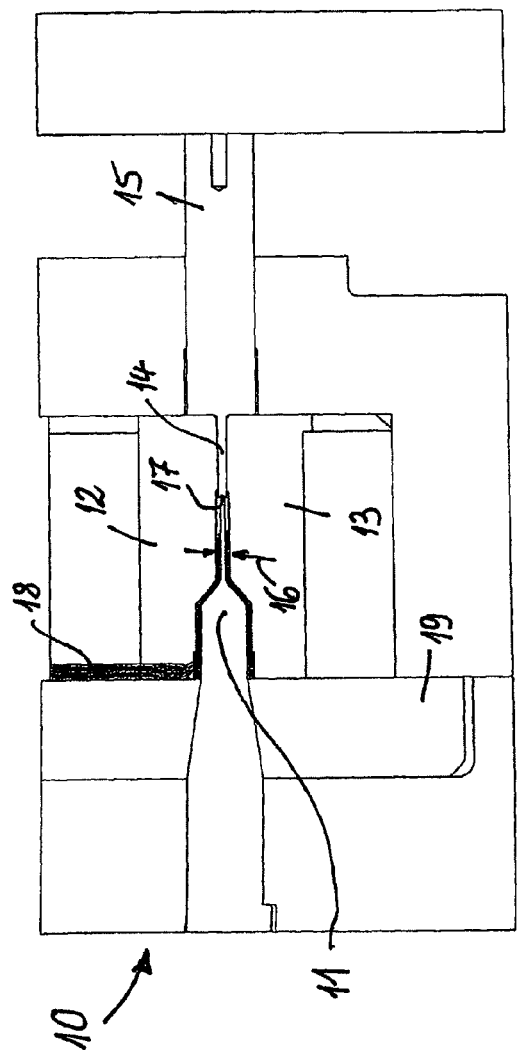

Further, in FIGS. 9 through 14 a support 14 with a holder 15 carrying it are discernible, according to FIGS. 9 and 10 first contacting the free narrow end 11b (cf. FIG. 14) of the contour core 11 at its narrow region 11a inside the mold 10 and fixing it, with the support 14 according to FIGS. 9 and 10 extending approximately to the point at which the end 4 of the measuring gap 2 is arranged in the finished cuvette.

By comparing FIGS. 9 and 10 with FIGS. 11 and 12 it becomes clear that this support 14 inside the injection mold 10 is retractable in reference to said contour core 11 in its direction of extension, which is also clearly discernible in FIGS. 11 and 12 by a distance 16a of the holder 15 from the mold parts 12 and 13, which distance 16a is not yet present in the arrangement according to FIGS. 9 and 10 prior to its retracting motion.

Here, it is discernible that the support 14 at its support end 14a, initially engaging the narrow region 11a of the contour core 11, comprises an approximately groove-shaped recess 17, which accepts the free edge 11b of the contour core 11 when supporting the contour core 11 and engages it in a form-fitting manner and slightly encompasses it and creates a bar 17a at the finished cuvette 1 below the measuring gap 2.

This way, said very narrowly measured region 11a of the contour core 11 is secured from any deflections or deformations by inflowing plastic until the plastic, after a partial filling approximately according to FIG. 10, ensures sufficient fixation even in this area of the contour core 11 such that then according to FIG. 11 the contour core 11 can be released by the support 14, i.e. said support can be retracted.

The carrying device or support 14 is here arranged, according to FIGS. 9 through 14, as a core-like intermediate piece between the mold parts 12 and 13 and completely fills the clear space existing between said mold parts 12 and 13, with said clear space being arranged adjacent to the distance of the mold parts 12 and 13 which the contour core 11 and its region 11a engage in the operational position.

The support 14 is therefore located in the extension of the region 11a and can also be retracted in said direction.

Here, it is also discernible that the thickness of the support 14, i.e. the distance between the mold parts 12 and 13 at said position, is smaller by a fraction of the thickness of the walls 6 limiting the measuring gap 2 than the distance of the mold parts 12 and 13 forming the exteriors of the walls 6 of the measuring gap 2. This difference in thickness is easily discernible in FIGS. 9 and 10, with the support 14 still slightly engaging the larger distance 16 between the mold parts 12 and 13, from which it later will be retracted.

Here, it is indicated in the figures that the thickness of the distance 14, i.e. the distance of the mold parts 12 and 13 in the region of this support 14 is lower by two half wall thicknesses of the walls 6 adjacent to the measuring gap 2 than the overall thickness of the measuring gap 2 with its two walls 6. Further it is discernible that the longitudinal center of the support 14 aligns and/or coincides with the contour core 11 and thus with the longitudinal center of the measuring gap 2 such that the support 14 still has a clear space of approximately one half of the thickness of a wall 6 at both sides in the contact area to the contour core 11. The support 14 is retracted by said overlapping region according to FIG. 11 during the progression of the process for producing the cuvette 1 such that it then releases a hollow transition between the walls 6 in the area of the end 4 for limiting the measuring gap 2, which according to FIG. 12 can also be filled with plastic after the retractive motion of the support 14.

First, when producing the cuvette 1 from plastic inside the injection mold 10, the contour core 11 is held at its end 11b by the support 14 and kept from deflection and plastic is injected through a feeding channel 18. After the plastic has formed a large portion of the cuvette, yet a remaining section of the walls 6 for the measuring gap 2 is still free from plastic, the support 14 is retracted by a small distance in order to release the transition of the two walls 6, which then is also filled with plastic.

After setting, a part of the injection mold 10 can be retracted with the mold parts 12 and 13 according to FIG. 13 or inversely the other part of the injection mold 10 comprising the doctor 19 can be retracted, and subsequently the cuvette 1 is now open at the outside but still remains arranged on the contour core 11.

According to FIG. 14 it is removed from the contour core 11 with the help of a doctor 19, adjustable in reference to the contour core 11, which first also forms the facial opening region or the opening edge of the cuvette 1.

The two mold parts 12 and 13 may also be formed by a single mold part, in which the exterior contour (AK) of the cuvette 1 is integrated at one side. In this case, the support 14 is located in an appropriate slot of a mold part comprising the cuvette contour such that the overall arrangement is equivalent to the arrangement shown in the figures and the production process of the cuvette can be executed in the manner described above, because the support 14 can then be retracted in a similar fashion into the slot continuing the cuvette contour.

Due to the production of the cuvette 1 from plastic, the above-mentioned recesses 7 for marking and differentiating the differently sized cuvettes 1 can also be arranged in a simple fashion as early as during the injection molding process.

In order to produce a cuvette 1 or a receptacle vessel for liquid or gaseous media for spectroscopic qualitative and/or quantitative analysis or measurement using a measuring region or measuring gap 2 that can be penetrated by radiation made from plastic by way of injection molding, a multi-part injection mold 10 is provided, which comprises the contours of the cuvette 1 to be produced and which is filled with initially liquid plastic in an injection molding device. Here, an interior cavity and/or the fill chamber 9 and the measuring gap 2 are formed and limited at the inside by a contour core 11 in the injection mold 10, with the thickness of said contour core 11 in the region 11a, by which the measuring gap 2 is produced, is limited to approximately one millimeter or less. At its edge or end 11b having the smallest dimension, the contour core 11 and its thin region 11a are held during the injection molding process first with the help of at least one support 14 and the end of the measuring gap 2, facing away from the opening 3 of the cuvette 1, i.e. its end 4, is formed such that at least one support 14 is retracted during the injection molding process to such an extent after the partial filling of the mold with plastic that, together with the end 11b of the contour core 11, it forms the lower continuation of the walls of the measuring gap 2. After this retracting motion or already during the retraction of at least one support 14 the injection molding process is continued until the entire hollow space inside the injection mold 10 is filled so that after the setting the then completed cuvette can be removed.

The invention claimed is:

1. A method for producing a cuvette (1) or a receptacle vessel for liquid or gaseous media for spectroscopic qualitative or quantitative analysis or measurement using a measuring region or measuring gap (2) that can be penetrated by radiation made from plastic, comprising:

injection molding liquid plastic into a multi-part injection mold (10), which comprises in an interior thereof a contour of the cuvette (1) or the receptacle vessel with an opening (3) and the measuring gap (2) in an injection molding device and, after the plastic has set, opening the injection mold (10) and removing the cuvette, and in the injection mold (10), forming and limiting an interior longitudinal cavity (9) and the measuring gap (2) at the interior using a contour core (11), which during the injection molding process is initially held by a support (14), a thickness of the contour core (11) in a region (11a) of the measuring gap (2) is limited to 1 millimeter or less, the contour core (11) is held by the support (14) at an end thereof comprising a smallest dimension, and an end of the measuring gap (2) facing away from the opening (3) or the vessel or the cuvette (1) is formed by removing or retracting the support (14) from the contour core (11) during the injection molding process, with the support (14) together with the end (11b) of the contour core (11) forming at its end a lower limit or continuation of the walls (6) of the measuring gap (2), and continuing the injection molding process during or after the removal or retraction of the support (14) until the hollow space released thereby has been filled, with the support (14) for the contour core (11) forming the measuring gap (2) being retracted in the direction of extension of the measuring gap (2) perpendicularly in reference to a later orientation of the radiation.

2. A method according to claim 1, wherein the support (14) arranged as a narrow intermediate piece between mold parts (12, 13) forming an exterior of the vessel or the cuvette (1) can be moved or retracted away from the contour core (11) in a separating region of the two mold parts (12, 13), and subsequently the injection molding process is concluded.

3. A device for producing a cuvette (1) or a receptacle vessel for liquid or gaseous media for at least one of spectroscopic qualitative or quantitative analyses or measurement using a measuring region or measuring gap that can be penetrated by radiation, the cuvette comprising an injection molded plastic part formed in a multi-part injection mold, an exterior contour (AK) of the cuvette (1) being arranged in a cavity of a mold or between two molds (12, 13) and an interior contour being formed by a contour core (11) arranged in or between the two mold parts (12, 13) and comprising a narrow region (11a) inside the injection mold (10) to form a measuring gap (2), the contour core (11) having a cross-sectional thickness of one millimeter or less plus or minus tolerances, and at least one support (14) for a free narrow end (11b) of the contour core (11) is arranged in a retractable fashion inside the injection mold (10) in reference to the contour core (11) in a direction of extension of the narrow region (11a) of the contour core (11), which during the filling process of the injection mold (10) is adapted to be retracted by a distance equal to a wall thickness of the limit of the interior or lower end of the measuring gap (2) or less and the support (14) is embodied as a core-like intermediate piece between the mold parts (12, 13) and fills a distance between said mold parts (12, 13) arranged adjacent to a distance (16) between the mold parts (12, 13), which the contour core (11) engages in an operational position.

4. A device according to claim 3, wherein the support(s) (14) of the contour core (11) comprises a concave or groove-shaped or slot-shaped recess (17) at a support end (14a) thereof, which when supporting the contour core accepts an end (11b) of the contour core (11) or encompasses it in a form-fitting fashion and forms an exterior contour of a limiting wall of the measuring gap (2) at an interior or lower end (4) thereof.

5. A device according to claim 4, wherein the support (14) is embodied as a core-like intermediate piece between the mold parts (12, 13) and fills a space between these mold parts (12, 13) arranged adjacent to the distance (16) between the mold parts (12, 13), which the contour core (11) engages in the operational position.

6. A device according to claim 1, wherein a thickness of the support (14) is lower by a fraction of a thickness of the walls (6) limiting the measuring gap (2) than the distance of the mold parts (12, 13) forming an exterior of the walls (6) of the measuring gap (2) or a slot forming a region of the measuring gap (2) in a mold part.

7. A device according to claim 3, wherein a thickness of the support (14) is lower by two half wall thicknesses of the walls (6) limiting the measuring gap (2) than an overall thickness of the measuring gap (2) with the walls (6) and that the longitudinal center of the support (14) is aligned to or coincides with a longitudinal center of the contour core (11) and thus with a longitudinal center of the measuring gap (2).

8. A cuvette produced in a method according to claim 1, wherein the cross-sectional thickness of the contour core is from one millimeter to one half of a millimeter.

9. A cuvette according to claim 8, wherein differently shaped geometric signs, grooves, notches, recesses or indentations (7) are provided at a wall (5), at a flange, or edge for marking different gap widths of the measuring gap (2) in order to differentiate between differently sized cuvettes (1).

10. A cuvette according to claim 8, wherein a central height of the cuvette (1) ranges from one half to three centimeters.

* * * * *